(12) United States Patent
Murphy et al.

(10) Patent No.: US 9,186,469 B2
(45) Date of Patent: *Nov. 17, 2015

(54) LOCATING DEVICE FOR NEEDLE INSERTION

(71) Applicant: Combat Medical Systems, LLC, Harrisburg, NC (US)

(72) Inventors: Christopher Murphy, Vass, NC (US); Corey Russ, Fayetteville, NC (US)

(73) Assignee: COMBAT MEDICAL SYSTEMS, LLC, Fayetteville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/524,895

(22) Filed: Oct. 27, 2014

(65) Prior Publication Data
US 2015/0045732 A1 Feb. 12, 2015

Related U.S. Application Data

(63) Continuation of application No. 13/539,165, filed on Jun. 29, 2012, now Pat. No. 8,870,820.

(51) Int. Cl.
*A61M 5/42* (2006.01)
*A61M 5/32* (2006.01)
*A61B 17/34* (2006.01)
(Continued)

(52) U.S. Cl.
CPC ............ *A61M 5/427* (2013.01); *A61B 17/3403* (2013.01); *A61B 19/54* (2013.01); *A61M 5/3287* (2013.01); *A61B 17/3415* (2013.01); *A61B 2017/3407* (2013.01); *A61B 2019/545* (2013.01); *A61B 2019/5437* (2013.01); *G01B 3/10* (2013.01)

(58) Field of Classification Search
CPC .............. A61M 5/427; A61M 5/3287; A61M 39/0208; A61B 17/3403; A61B 2017/3411; G01B 3/10; G01B 5/14; G01B 3/14; G01B 3/02; G01D 5/00; G01D 21/00; A47G 1/205; B43L 13/002; B43L 7/10
USPC .......................................................... 604/116
See application file for complete search history.

(56) References Cited

U.S. PATENT DOCUMENTS 2,245,350 A * 6/1941 Marshall .......................... 33/511
2,456,676 A * 12/1948 Chowns .......................... 33/486
(Continued)

FOREIGN PATENT DOCUMENTS

DE 10 2007 042 524 A1 3/2009
WO WO 02/068028 9/2002

*Primary Examiner* — Manuel Mendez
(74) *Attorney, Agent, or Firm* — Knobbe, Martens, Olson & Bear, LLP

(57) ABSTRACT

A template for locating a proper place for inserting a needle. The template has two reference indicators that are placed on a person's body and an elongated body, with incremental markings on each side of the elongated body, that moves relative to the two reference indicators. The incremental markings on each side of the elongated body can be scaled differently. One reference indicator is placed over the clavicle and the other is placed over the nipple on the same lateral side. The elongated body is moved until the reference indicators are each lined up with equivalent incremental markings on each half of the elongated body. When the reference indicators are lined up with matching incremental markings, a fixed target, positioned between the two sets of incremental markings, will indicate a proper location for inserting a pneumothorax relief needle.

16 Claims, 2 Drawing Sheets

(51) Int. Cl.
*A61B 19/00* (2006.01)
*G01B 3/10* (2006.01)

(56) References Cited

U.S. PATENT DOCUMENTS

| | | | | |
|---|---|---|---|---|
| 3,456,353 A | * | 7/1969 | Iams | 33/429 |
| 4,241,510 A | * | 12/1980 | Radecki | 33/613 |
| 4,593,698 A | | 6/1986 | Athans | |
| 4,930,525 A | | 6/1990 | Palestrant | |
| 4,969,273 A | * | 11/1990 | Richards | 33/613 |
| 5,098,383 A | | 3/1992 | Hemmy et al. | |
| 6,036,632 A | | 3/2000 | Whitmore, III et al. | |
| 6,574,880 B2 | * | 6/2003 | Lombardo | 33/666 |
| 7,185,442 B2 | * | 3/2007 | Grillo | 33/613 |
| 7,503,126 B2 | * | 3/2009 | Robins | 33/613 |
| 7,690,129 B2 | * | 4/2010 | Bender | 33/613 |
| 8,075,525 B2 | | 12/2011 | Yang | |
| 8,133,201 B1 | | 3/2012 | Hurtado | |
| 8,870,820 B2 | * | 10/2014 | Murphy et al. | 604/116 |
| 2010/0015590 A1 | | 1/2010 | Kiss | |

* cited by examiner

LOCATING DEVICE FOR NEEDLE INSERTION

RELATED APPLICATIONS

This is a continuation of U.S. patent application Ser. No. 13/539,165, filed on Jun. 29, 2012, and entitled "Locating Device for Needle Insertion," the entirety of which is hereby incorporated herein and made part of this specification for all that it discloses.

BACKGROUND

1. Field of the Invention

The inventions relate generally to locating zones and specifically locating physiological zones.

2. Related Art

A condition known as a pneumothorax, or "collapsed lung," can occur with a penetrating wound. The outer portion of the lung is composed of two tissue layers: the internal visceral pleura that cover the lungs, and the external parietal pleura that is attached to the chest wall. The space between the visceral and parietal pleura is known as the pleural space. Under normal conditions, the visceral and parietal pleura are nearly flush against one another with the pleural space usually containing only a thin layer of pleural fluid. However, when an aperture to the pleural space is created by a penetrating chest wound, air or fluids can enter the pleural space and create a pocket that compresses the inner portion of the lung, making breathing extremely difficult.

Pneumothoracies are generally classified into two types: tension and non-tension. The latter can occur with trauma, various illnesses, or even spontaneously. It can lead to chest pain and difficulty breathing because the lung is incapable of expanding fully, but it is generally of lesser concern than tension pneumothorax, which is a medical emergency. A tension pneumothorax occurs when a penetrating chest wound effectively forms a one-way valve into the chest cavity that allows airflow into the pleural space while preventing airflow out. In a tension pneumothorax, each inhalation traps air in the chest, increasing pressure on the lungs and ultimately causing them to collapse. In some cases, one lung can be pushed into the heart and into the other lung, interfering with the functions of these vital organs. As the blood vessels of the lung are compressed, the vascular pressure increases and puts pressure on the right ventricle of the heart, possibly leading to cardiac failure.

One treatment for a pneumothorax condition is chest decompression with needle thoracostomy in which a needle is inserted into the second rib space in the mid-clavicular line. This procedure can relieve the build-up of pressure in the lungs and provide relief to the patient. There are some positions on the chest that are better than others for insertion of the needle. However, when there are increased pressures on the medical personnel performing the procedure, such as in combat situations, EMTs responding to the scene of an accident, or emergency room staff with multiple demands, the needle may be inadvertently placed in an incorrect location. This can lead to a misdiagnosis of the extent of the injuries a patient suffers, prolonged discomfort of the patient, and additional injury to the patient. There is a need for a quick and simple way to ensure the proper insertion of a needle into a patient's body.

SUMMARY OF THE DISCLOSURE

A needle locating device provides users with an easy-to-use and reliable way to locate a proper zone in which to insert a needle. In some embodiments, medical personnel, and other persons, can use the device under stressful situations to identify a plurality of reference points on a human patient and slide an elongated body until a reference marking is displayed in a reference window. The marker will then indicate a proper location for inserting a needle, such as a pneumothorax relief needle.

DETAILED DESCRIPTION OF THE PREFERRED EMBODIMENTS

A needle locating device can utilize one or more physiological regions on a patient as inputs or markers to aid in determining a suitable zone in which a needle, such as a pneumothorax relief needle, can be inserted into a patient. In some embodiments, the locating device can comprise one or more reference portions that are configured to be positioned adjacent to, on, in, or around one or more anatomical structures. The one or more reference portions can be connected, either directly or indirectly, to an insertion indicator portion that designates a zone on the body for inserting a needle. In some embodiments, the relative locations of the reference and/or insertion indicator portions with respect to each other can be adjusted. In some embodiments, an adjustment indicator portion can be configured to provide information regarding the adjustable positions of the reference or insertion indicator portions.

Figure 1:
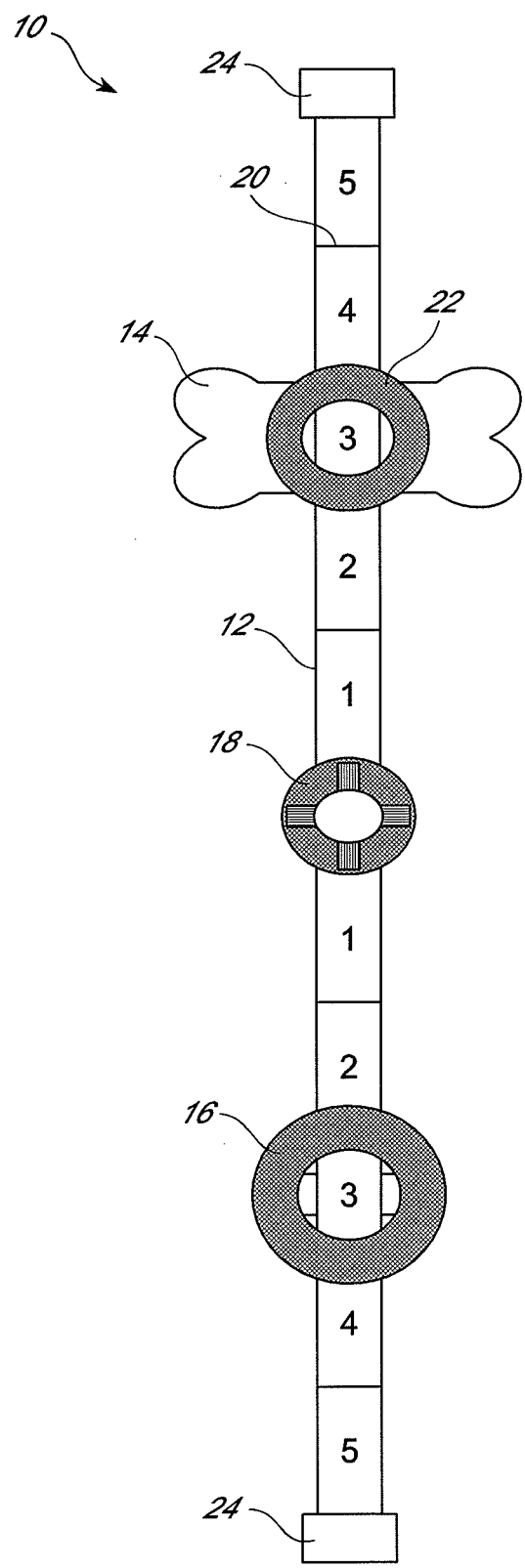
FIG. 1 is a perspective view of a pneumothorax relief needle locating device according to an embodiment of the invention.
Figure 2:
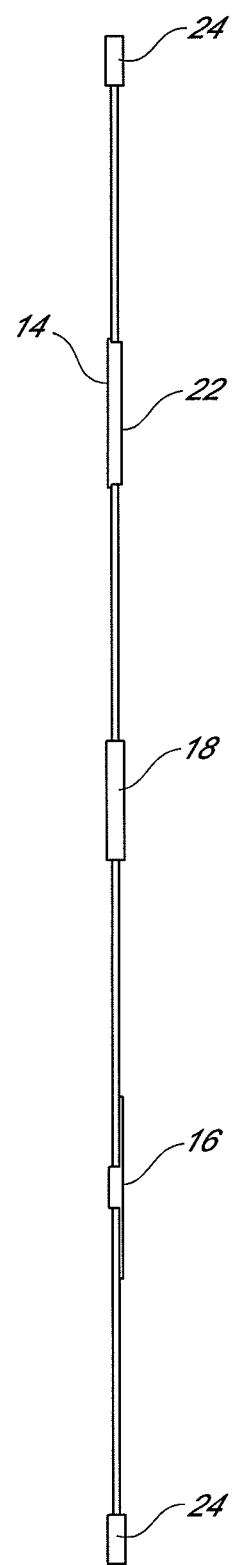
FIG. 2 is a side view of pneumothorax relief needle locating device of FIG. 1.
Figure 3:
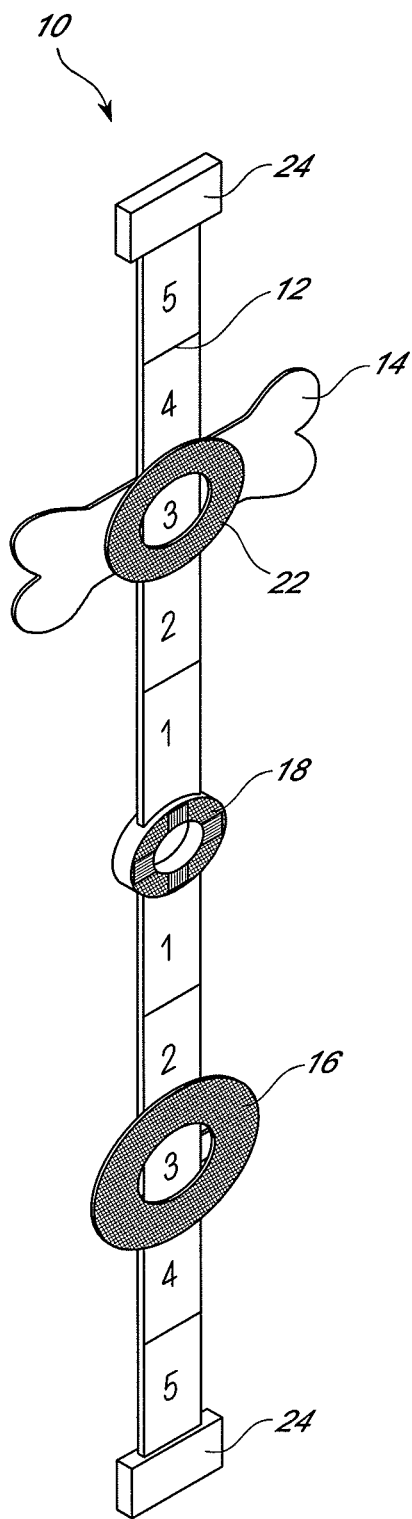
FIG. 3 is a perspective view of a pneumothorax relief needle locating device according to another embodiment of the invention.
Figure 4:
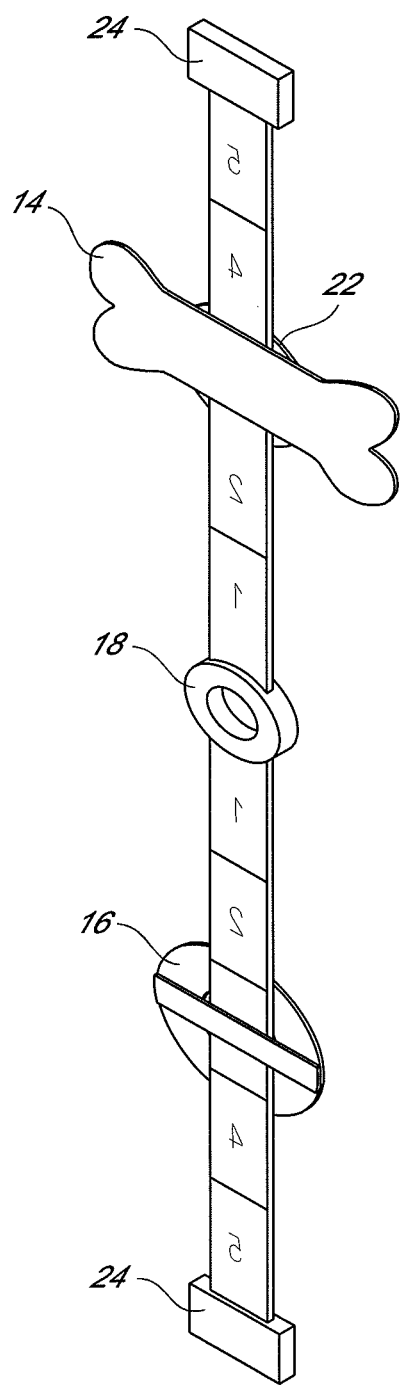
FIG. 4 is a rear perspective view of the pneumothorax relief needle locating device of FIG. 3.

In some embodiments, the pneumothorax relief needle locating device can comprise a pneumothorax relief needle template, as indicated generally by the numeral 10 in FIG. 1. The template can include an elongated body 12 with incremental markings 20 to indicate an adjustment value (which can correspond in some embodiments to the approximate relative or absolute distance from an insertion indicator portion, such as a fixed target 18). In some embodiments, the fixed target 18 can be located at the substantial midpoint of the elongated body 12. In some embodiments, the fixed target 18 can be positioned closer to one end of the elongated body 12 than the other end. Two reference indicators 14, 16 can be attached to the elongated body 12 such that each indicates its position in relation to the incremental markings 20. In the illustrated embodiment, the incremental markings 20 are part of an adjustment indicator portion. The adjustment indicator portion can be configured in other ways.

In some embodiments, the elongated body 12 can be made from semi-rigid plastic. In some embodiments, at least a portion of the needle locating device can be transparent. In some embodiments, the incremental markings 20 on the elongated body 12 can be scaled to substantially correspond to the number of inches from the fixed target 18. In some embodiments, the incremental markings 20 can be scaled to substantially correspond to the number of centimeters from the fixed target 18. In some embodiments, a plurality of insertion indicator portions can be attached to the needle locating device, such as when the reference portions are not movable.

In some embodiments, the scale of the incremental markings 20 can differ on each side of the fixed target 18 such that equivalent numbers on each side of the fixed target 18 will be a different distance from the fixed target 20. In some embodiments, one or more adjacent pairs of incremental markings 20 on one side of the fixed target 18 are slightly further apart than one or more adjacent pairs of incremental markings 20 on the other side of the fixed target 18. In some embodiments, the scale on the upper portion of the needle locating device can be larger than the scale on the lower portion. In other embodiments, the scale on the lower portion can be larger than the scale on the upper portion. For example, in some embodiments, each incremental marking 20 on the lower portion of the needle locating device can generally correspond to a distance of greater than one inch (e.g., about 1.05 inches), while each incremental marking 20 on the upper portion of the needle locating device can generally correspond to a distance of less than one inch (e.g., about 0.9 inches). This can result in equivalent incremental markings 20 on the upper and lower portions of the elongated body 12 being a different absolute distance from the fixed target 18. In some embodiments the difference in scale between the upper and lower portions can be greater or less than this example.

In some embodiments, the fixed target 18 can be placed on the elongated body 12 so as to be substantially at the midpoint of the elongated body 12. In some embodiments, the fixed target 18 can be placed such that it is closer to one end of the elongated body than the other end. The fixed target 18 functions as an insertion point indicator to let a user know the proper location to insert the pneumothorax relief needle. The insertion indicator portion can comprise an aperture through which the skin of the patient can be marked or through which a needle can be inserted. In some embodiments, the aperture is sufficiently wide to permit the passage of a pneumothorax relief needle and hub so that the locating device can be removed from the patient after the pneumothorax relief needle has been inserted into the chest of a patent. For example, in a first step, the locating device can be positioned on a patient; in a second step, the needle can be inserted through the aperture and into the patient; and in a third step, the locating device can be removed from the patient with the needle hub passing through the aperture upon removal of the locating device. In some embodiments, the insertion indicator portion includes a marking device for marking the needle-insertion location on a patient. In some embodiments, the fixed target 18 can be attached to the elongated body 12 such that it provides a hole, notch, or other indication in or on the elongated body 12 to indicate the proper location for insertion of a pneumothorax relief needle. In some embodiments, the elongated body 12 can comprise a plurality of sections which are each attached to the fixed target 18 and each with corresponding incremental markings. The scale of the incremental markings on each section can determine the length of that section relative to the other section and can determine the position of the fixed target 18 in relation to the elongated body 12 as a whole. The fixed target 18 can provide a hole, notch, or other indication to indicate the proper location for insertion of a pneumothorax relief needle.

In the illustrated embodiment, the reference portions and the insertion indicator portion are all positioned in a substantially co-linear path. In some embodiments, one or more portions can be non-colinear with one or more other portions. In the illustrated embodiment, the locating device is not required to wrap around the body or to contact the underside or lateral sides of the body, thereby avoiding the need to unnecessarily roll, lift, or otherwise move an injured person in order to properly position the locating device. In some embodiments, one or more portions of the locating device can be configured to wrap around a body portion or to contact the sides or back of the body.

The two reference indicators 14, 16 can be attached to the elongated body 12 such that the reference indicators 14, 16 are movable in relation to the elongated body 12. The reference indicators can be attached via hooks, straps, material that wraps around the elongated body 12, or via any other method that allows the reference indicators to move in relation to the elongated body 12.

In some embodiments, a reference indicator 14, 16 includes a position indicator 22 that indicates the relative position of that reference indicator with respect to the fixed target 18. In some embodiments, this is accomplished by means of an opening on the reference indicator so that the incremental markings 20 can be viewed to determine the approximate relative distance that the reference indicator 14, 16 is from the fixed target 18. In some embodiments, the position indicator 22 can be a notch in the reference indicator to indicate the proper place to measure the relative distance to the fixed target 18 by reference to the incremental markings 20. In some embodiments, a position indicator 22 can be an identified edge of the reference indicator 14, 16 or any other such device that enables a user to identify the approximate relative distance the reference indicator 14, 16 is from the fixed target 18.

In some embodiments, the incremental markings 20 can be visually distinct from each other to better aid the user in matching the equivalent markings on each marked portion of the elongated body 12. In some embodiments the visual distinctions can correspond to a plurality of different colors, patterns, designs, or other visually distinctive marking. These visual distinctions can be replicated on each marked portion of the elongated body 12 so that the same visual distinction is used for the equivalent marking on each marked portion of the elongated body 12. For example, in some embodiments, the first unit of distance from the fixed target 18 can be red on both sides of the fixed target 18; the second unit of distance from the fixed target 18 can be orange on each side; the third unit of distance can be yellow; etc. In some embodiments, the user can quickly determine whether the reference indicators 14, 16 are aligned with equivalent markings on the elongated body 12 by reference to the visual distinctions. In some embodiments, differing patterns, shapes, or other designs may be used in the same or similar manner, rather than or in addition to different colors.

In the illustrated embodiment, the location of the insertion indicator portion is fixed in relation to the needle locating device and the reference portions are movable. In some embodiments, the insertion indicator portion is movable and the reference portions are fixed, such as when a plurality of different-size needle locating devices are available to accommodate patients with varying physiological characteristics. In some embodiments, the elongated body 12 comprises at least two portions that are movable with respect to each other. In some embodiments, these movable portions can nest, one within the other, and/or can expand or contract with respect to the insertion indicator portion in tandem, at generally the same increments or at different increments depending on the desired scale of each portion relative to the other portion. Many other combinations of fixation and movability for various components can be used.

Each reference indicator corresponds to a certain part of a human body over which that indicator is to be placed. One or more of the reference indicators can comprise a transparent portion to permit viewing of at least a portion of a body part through the reference indicator. The reference indicators can be made to take on any shape. In some embodiments, the reference indicators 14, 16 can be shaped to correspond to one or more areas of a human body or to otherwise provide a symbol to remind the user where to position the reference indicators 14, 16. For example, in some embodiments, one of the reference indicators 14 can be shaped similar to a clavicle or bone to correspond to placement substantially over, or in line with, the clavicle on a human patient. Additionally, in some embodiments, one of the reference indicators 16 can be substantially round in shape to correspond to placement substantially on or over the nipple of a human patient.

In some embodiments, one or more of the reference indicators 14, 16 can contain an adhesive backing to aid in affixing the reference indicator 14, 16 to the proper position on the human body. The adhesive backing can be protected with a protective covering until ready for use when the adhesive backing can be exposed by removing the protective covering. The reference indicator 14, 16 can then be fixed to the appropriate location in relation to the human body with the aid of the adhesive backing.

In some embodiments, end caps 24 can be placed at each end of the elongated body 12 to assist in preventing the reference indicators 14, 16 from sliding off of the elongated body 12. This can help keep the pneumothorax relief needle template 10 ready for quick use when a need arises.

In some embodiments, written directions can be included on the front or back of one or more of the reference indicators 14, 16. In some embodiments, written directions can be included on the front or back of the elongated body 12. In some embodiments, written directions can be included on another part of the template 10.

In use, some embodiments of the pneumothorax relief needle template 10 can be used by medical personnel, or other persons, to locate the proper place to insert a needle. In some embodiments, the template 10 is placed over the torso of a human body such that a first reference indicator 14 is lined up with, or over, the patient's clavicle on the side of the body with a collapsed lung condition. In some embodiments, the first reference indicator 14 can have a shape that resembles a bone. In some embodiments, the first reference indicator 14 can have an adhesive backing that, when exposed, assists in securing the first reference indicator 14 in line with, or over, the patient's clavicle. With the first reference indicator 14 placed in line with, or over, the patient's clavicle, a second reference indicator 16 can be placed over the nipple of a patient's breast which is on the same side of the body that the first reference 14 indicator was placed. In some embodiments, the second reference indicator 16 can be shaped substantially round. In some embodiments, the second reference indicator 16 can have an adhesive backing that, when exposed, assists in securing the second reference indicator 16 over the patient's nipple. In some embodiments, when both reference indicators are properly placed on the patient, the elongated body can slide until incremental markings 20 of approximate equal value appear in both reference windows 22. When the value of the incremental marking 20 displayed in both reference windows 22 match each other, the fixed target indicates a proper location for inserting a pneumothorax relief needle.

In some embodiments, end caps 24 can be useful to prevent the elongated body 12 from sliding too far and becoming detached from one or more of the reference indicators 14, 16. In some embodiments, the end caps 24 can be eliminated and the elongated body 12 can be inserted into the reference indicators 14, 16, or otherwise placed in reference to the reference indicators 14, 16 without attachment, such that the reference windows 22 can indicate when the incremental markings 20 corresponding to each reference window 22 are approximately equal. The fixed target will then indicate a proper location for inserting a pneumothorax relief needle.

The invention claimed is:

1. A medical template for locating a proper insertion point for a needle on a torso of a patient, the medical template comprising:
   a main body comprising a first region and a second region, and an insertion point indicator configured to indicate a body zone where a needle can be inserted into a patient's torso to provide a medical treatment;
   a first reference indicator movably attached to the main body, wherein the first reference indicator is configured to be positioned near a first reference region on a patient's body;
   a second reference indicator movably attached to the main body, wherein the second reference indicator is configured to be positioned near a second reference region on a patient's body, and wherein the relative locations of either of the first reference indicator or the second reference indicator can be adjusted relative to the insertion point indicator; and
   markings on the medical template that are configured to indicate proper spacing of the first reference indicator and the second reference indicator with respect to the insertion point indicator for the medical treatment when the first reference indicator is positioned near the first reference region and the second reference indicator is positioned near the second reference region on the patient's body.

2. The medical template of claim 1, wherein the insertion point indicator is a hole, notch or other opening located at a common reference position for both the first reference indicator and the second reference indicator.

3. The medical template of claim 1, wherein the first reference indicator and the second reference indicator are slideably attached to the main body.

4. The medical template of claim 3, further comprising an end cap on an end of the main body to prevent a reference indicator from sliding off of the elongated body.

5. The medical template of claim 1, wherein the main body is elongated.

6. The medical template of claim 1, wherein the markings are scaled.

7. The medical template of claim 6, wherein the markings are scaled closer together on a first region than on a second region.

8. The medical template of claim 1, wherein at least one of the first reference indicator or the second reference indicator has a shape that corresponds to an anatomical reference.

9. The medical template of claim 8, wherein the shape is a bone shape.

10. The medical template of claim 1, wherein at least one of the first reference indicator or the second reference indicator has an adhesive region to fix the reference indicator to the proper position on a patient's body.

11. The medical template of claim 1, wherein the markings comprise different visual elements that correspond to an amount of units that a particular marking is away from the body zone where the needle is to be inserted.

12. The medical template of claim 11, wherein the visual elements comprise different colors to indicate the amount of units that a particular marking is away from the body zone.

13. The medical template of claim 11, wherein the visual elements comprise different patterns to indicate the amount of units that a particular marking is away from the body zone.

14. A method of determining a proper insertion point for a pneumothorax-relief needle on a chest of a patient with a medical template, the method comprising:
- placing a first reference indicator of the medical template at a first location on a torso of the patient;
- placing a second reference indicator of the medical template at a second location on the torso of the patient which is on the same side where the first reference indicator is placed; and
- adjusting the medical template, which comprises a set of markings, such that a marked insertion point is positioned at a location on the patient's torso where a pneumothorax-relief needle can be inserted to provide pneumothorax relief to the patient.

15. The method of claim 14, wherein the first reference indicator is fixed to a region of the torso by adhesion.

16. The method of claim 15, wherein the second reference indicator is fixed to a region of the torso by adhesion.

\* \* \* \* \*